US008609724B2

(12) United States Patent
Michelakis et al.

(10) Patent No.: US 8,609,724 B2
(45) Date of Patent: Dec. 17, 2013

(54) METHOD OF TREATING CANCER USING DICHLOROACETATE

(76) Inventors: Evangelos Michelakis, Edmonton (CA); Stephen Archer, La Grange, IL (US)

(*) Notice: Subject to any disclaimer, the term of this patent is extended or adjusted under 35 U.S.C. 154(b) by 502 days.

(21) Appl. No.: 11/911,299

(22) PCT Filed: Apr. 11, 2006

(86) PCT No.: PCT/CA2006/000548
§ 371 (c)(1),
(2), (4) Date: Dec. 1, 2008

(87) PCT Pub. No.: WO2006/108276
PCT Pub. Date: Oct. 19, 2006

(65) Prior Publication Data
US 2009/0118370 A1    May 7, 2009

Related U.S. Application Data

(60) Provisional application No. 60/669,884, filed on Apr. 11, 2005.

(51) Int. Cl.
*A61K 31/19* (2006.01)

(52) U.S. Cl.
USPC ............................................. 514/557

(58) Field of Classification Search
USPC ............................................. 514/557
See application file for complete search history.

(56) References Cited

U.S. PATENT DOCUMENTS

| | | | | |
|---|---|---|---|---|
| 3,431,299 A | * | 3/1969 | Levi et al. ........................ | 562/567 |
| 4,631,294 A | * | 12/1986 | Barsan .......................... | 514/557 |
| 8,071,645 B2 | | 12/2011 | Newell et al. | |
| 8,293,240 B2 | | 10/2012 | Newell et al. | |
| 2009/0209618 A1 | * | 8/2009 | Dang et al. .................. | 514/44 A |
| 2009/0258064 A1 | | 10/2009 | Newell et al. | |
| 2010/0330087 A1 | | 12/2010 | Newell et al. | |
| 2012/0128724 A1 | | 5/2012 | Newell et al. | |

FOREIGN PATENT DOCUMENTS

| | | |
|---|---|---|
| WO | WO2004/111199 A2 | 12/2004 |
| WO | 2006/042062 A2 | 4/2006 |
| WO | 2006/108276 A1 | 10/2006 |
| WO | WO2012/135632 A2 | 10/2012 |

OTHER PUBLICATIONS

Saghir et al., Environmental Health Perspectives, 1101(8); (2002); 757-763.*
International Agency for Research on Cancer 84, (2004) p. 359 (now pp. 1-3).*
American Chemical Society (2009) 1-7.*
Sutendra et al. Mitochondria and Cancer (2009) 251-264.*
Summerhayes Proc. Natl. Acad. Sci (1982) 79; 5292-5296.*
Gogvadze et al. Seminars in Cancer biology 19 (2009) 57-66.*
Costantini, P. et al.: "mitochondrion as a novel target of anticancer chemotherapy," Journal of the national cancer institute, vol. 92 No. 13, Jul. 5, 2000, Oxford university press 1042-53, See whole document.
Fantin, V.R. et al.: "A novel mitochondriotoxic small molecule that selectively inhibits tumor cell growth," Cancer Cell vol. 2, Jul. 2002, Cell Press pp. 29-42, See whole document.
McMurtry M.S. et al. "Dichloroacetate prevents and reverses pulmonary hypertension by inducing pulmonary artery smooth muscle cell apoptosis" Circulation Research, vol. 95, 2004 American Heart Association Inc. pp. 830-840, See whole document.
Yang, J. & Smith, R.A.: "The effect of dichloroacetate on the physphorylation of mitochondria proteins" Biochemical and Biophysical Research Communication, vol. 111 No. 3, 1983, Academic Press Inc. pp. 1054-1058.
Nagy, G. et al.: "T cell activation-induced mitochondrial hyperpolarization is mediated by $Ca^{+2}$ and redox-dependent production of nitric oxide" Journal of Immunology, vol. 171, 2003, The Am. Assoc. of Immunologists Inc. pp. 5188-5197, see whole document.
Pal, S. et al. "Mediation of neuronal apoptosis by Kv2.1-encoded potassium channels" The Journal of Neuroscience, vol. 23 No. 12, Jun. 15, 2003, Society for Neuroscience, pp. 4798-4802, See whole document.
International Search Report Published as WO 2006/108276A1.
Caldwell JC, Keshava N, Environ Health Perpect, Sep. 2006; 114(9):1457-63. Key issues in the modes of action and effects of trichloroethylene metabolites for liver and kidney tumorigenesis.
Pereira MA, Wang W, Kramer PM, Tao L, Toxicol Sci. Feb. 2004; 77(2):243-8. Epub Dec. 2, 2003 Prevention by methionine of dichloroacetic acid-induced liver cancer and DNA hypomethylation in mice.
Carter JH, Carter HW, Deddens JA, Hurst BM, George MH, DeAngelo AB, Environ Health Perspect, Jan. 2003:111(1):53-64. A 2-year dose-response study of lesion sequences during hepatocellular carcinogenesis in the male B6C3F(1) mouse given the drinking water chemical dichloroacetic acid.
Lingohr MK, Bull RJ, Kato-Weinstein J, Thrall BD, Toxicol Sci. Aug. 2002;68(2):508-15, Dichloroacetate simulates glycogen accumulation in primary hepatocytes through an insulin-independent mechanism.
Lash LH, Parker JC, Pharmacol Rev. Jun. 2001;53(2):177-208, Hepatic and renal toxicities associated with perchloroethylene.

(Continued)

Primary Examiner — Shirley V Gembeh
(74) Attorney, Agent, or Firm — Anita Nador; Carol Miernicki Steeg

(57) ABSTRACT

The invention relates to the use of dichloroacetate and chemical equivalents thereof for the treatment of cancer by inducing apoptosis or reversing apoptosis-resistance in a cell Preferably, the dosage is 10-100 mg/kg Preferably, sodium dichloroacetate is used. The dichloroacetate may optionally be given in combination with a pro-apoptotic agent and/or a chemotherapeutic agent Preferably, the cancers treated are non-small cell lung cancer, glioblastoma and breast carcinoma.

20 Claims, 7 Drawing Sheets

(56) References Cited

OTHER PUBLICATIONS

Bull RJ, Environ Health Perspect, May 2000;108 Suppl 2:241-59. Mode of action of liver tumor induction by trichloroethylene and its metabolites, trichloroacetate and dichloroacetate.

Andersen ME, Meek ME, Boorman GA, Brusick DJ, Cohen SM, Dragan YP, Frederick CB, Goodman JI, Hard GC, O'Flaherty EJ, Robinson DE, Toxicol Sci. Feb. 2000;53(2):159-72. Lessons learned in applying the U.S. EPA proposed cancer guidelines to specific compounds.

Boorman GA, Environ Health Perspect. Feb. 1999; 107 Suppl 1:207-17. Drinking water disinfection byproducts: review and approach to toxicity evaluation.

Elfarra AA, Krause RJ, Last AR, Lash LH, Parker JC, Drug Metab Dispos. Aug. 1998;26(8):779-85. Species- and sex-related differences in metabolism of trichloroethylene to yield chloral and trichloroethanol in mouse, rat, and human liver microsomes.

Fields AL, Wolman SL, Halperin ML, Cancer. Apr. 15, 1981;47(8):2026-9. Chronic lactic acidosis in a patient with cancer: therapy and metabolic consequences.

Dyck, A Haromy, K. Hashimoto, ED Michelakis, Circulation, 2004, Am Heart Assoc., Dichloroacetate prevents and reverses pulmonary hypertension by inducing pulmonary artery smooth muscle cell apoptosis.

ED Michelakis, MS McMurtry, XC Wu, JRB Dyck, R, Circulation, 2002, Am Heart Assoc., Dichloroacetate, a metabolic modulator, prevents and reverses chronic hypoxic pulmonary hypertension in rats: role of increased expression and activity of voltage.

ED Michelakis, Circulation research, 2006, Am Heart Assoc., Spatiotemporal diversity of apoptosis within the vascular wall in pulmonary arterial hypertension: heterogeneous BMP signaling may have therapeutic implications.

S Bonnet, L Puttagunta ED Michelakis, Journal of Clinical, 2005, Am Soc Clin Investig., Gene therapy targeting survivin selectively induces pulmonary vascalar apoptosis and reverses pulmonary arterial hypertension.

ZI Pozeg, ED Michelakis, MS McMurtry, B Theband, Circulation, 2003, Am Heart Assoc., In vivo gene transfer of the O2-sensitive potassium channel Kv1, 5 reduces pulmonary hypertension and restores hypoxic pulmonary vasoconstriction in chronically.

K Hashimoto, G Harry, ED Michelakis, Cirulation, 2004, Am Heart Assoc., Preferential expression and function of voltage-gated, O2-sensitive K+ channels in resistance pulmonary arteries explains regional heterogeneity in hypoxic.

ED Michelakis, W Tymchak, M Noga, L. Webster, XC, Circulation, 2003, Am Heart Assoc., Long-term treatment with oral sildenafil is safe and improves functional capacity and hemodynamics in patients with pulmonary arterial hypertension.

ED Michelakis, I Rebeyka, XC Wu, A Nsair, B, Circulation, 2002, Am Heart Assoc, O2 sensing in the human ductus arteriosus: regulation of voltage-gated K+ channels in smooth muscle cells by a mitochondrial redox sensor.

TA Hopkins, S Bonnet, ED Michelakis, ME Young, M, Circulation, 2006, Am Heart Assoc. Absence of malonyl coenzyme A decarboxylase in mice increases cardiac glucose oxidation and protects the heart from ischemic injury.

Chen, Lan Bo, Mitochondrial Membrane Potential in Living Cells, Ann. Rev. Cell Biol., 1988, 4:155-181, Dana-Farber Cancer Institute, Harvard Medical School, Boston, Massachusetts.

Levi, Irving, et al., Serine Derivative with Antitumor Activity, Science, 1959, 131:666, Research Laboratories, Charles E. Frosst and Co., Montreal, Canada.

Harper, M.E., et al.. "Characterization of a novel metabolic strategy used by drug-resistant tumor cells," The FASEB Journal, vol. 16, 1550-1557 (2002).

* cited by examiner

METHOD OF TREATING CANCER USING DICHLOROACETATE

CLAIM OF BENEFIT OF FILING DATE

The present application claims the benefit of the filing date of PCT Application Serial No. PCT/CA2006/000548, (filed Apr. 11, 2006) (published as WO 06/108276) and U.S. Ser. No. 60/669,884 (filed Apr. 11, 2005), the contents of which are hereby incorporated by reference in their entirety for all purposes.

FIELD OF THE INVENTION

The invention relates to the use of dichloroacetate and obvious chemical equivalents thereof in the treatment of cancer. Related uses and diagnostic and screening methods are also included in one aspect of the present invention.

BACKGROUND OF THE INVENTION

Most cancers are characterized by a resistance to apoptosis that makes them prone to proliferation and resistant to most cancer therapies. Most of the available cancer treatments aim to induce apoptosis but are highly toxic. There are two main categories of apoptosis: the receptor-mediated and the mitochondria-dependent apoptosis. Mitochondria-dependent apoptosis is not very well studied and only recently have the mitochondria been viewed as anything more than an organelle that produces energy. As such there is a need for a cancer therapy that can overcome apoptosis resistance in cancer cells.

SUMMARY OF THE INVENTION

A cell can become resistant to apoptosis in a variety of ways one of which is altering its metabolism and having hyperpolarized mitochondria. Since apoptosis is initiated by depolarization of mitochondria, the more hyperpolarized a mitochondrion is, the further it is from the depolarization threshold and the more resistant it is to the initiation of apoptosis.

In one embodiment the present inventors have surprisingly found that one can modulate mitochondrial function to treat cancer. In one embodiment, the present invention provides a method for inducing apoptosis in cancer. In another embodiment, the inventors provide a method for inducing apoptosis in cancer but not normal cells. In another embodiment, the invention provides a method of reversing apoptosis resistance in cancer cells, such as cancer cells with hyperpolarized mitochondria. In one embodiment, the method comprises administering to cancer cells, in one embodiment cells having or suspected of having hyperpolarized mitochondria, an effective amount of dichloroacetate or salts thereof or obvious chemical equivalents thereof.

In one embodiment, the dichloroacetate or obvious chemical equivalent thereof is administered in combination with another pro-apoptotic agent and/or chemotherapeutic agent, and/or other cancer therapy.

In one embodiment, the invention provides a method for inducing apoptosis and/or reversing apoptosis resistance in a cancer cell, comprising administering to the cell an effective amount of dichloroacetate or obvious chemical equivalent thereof. In another embodiment, the invention provides a method for inhibiting proliferation of cancer cells, comprising administering to the cells an effective amount of dichloroacetate or obvious chemical equivalent thereof. In another embodiment, the invention provides a method of decreasing survivin in a cancer cell, comprising administering to the cell an effective amount of dichloroacetate or obvious chemical equivalent thereof. In another embodiment, the invention provides a method of increasing Kv1.5 protein in a cancer cell comprising administering to the cell an effective amount of dichloroacetate or obvious chemical equivalent thereof. In another embodiment, the invention provides a method of increasing AIF in a cancer cell comprising administering to the cell an effective amount of dichloroacetate or obvious chemical equivalent thereof. In another embodiment, the invention provides a method of increasing $H_2O_2$ in a cancer cell comprising administering to the cell an effective amount of dichloroacetate or obvious chemical equivalent thereof. In another embodiment, the methods of the invention affects cancer cells, but normal or non-cancerous cells are not affected by the treatment with dichloroacetate or obvious chemical equivalent thereof.

In one embodiment, the present invention provides a method for treating a cancer. In another embodiment, the invention provides a method of treating a cancer associated with hyperpolarized mitochondria. In another embodiment the invention provides a method of treating cancer by restoring mitochondrial membrane potential ($\Delta\Psi m$) (essentially depolarizing the hyperpolarized cancer cell mitochondria). This molecular metabolic therapy is accomplished by administering to a patient in need thereof a therapeutically effective amount of dichloroacetate or obvious chemical equivalent thereof. In another embodiment, the invention provides a use of dichloroacetate or obvious chemical equivalent thereof in the treatment of cancer.

In one embodiment, the dichloroacetate is a salt of dichloroacetic acid. In another embodiment, the dichloroacetic acid is a sodium salt of dichloroacetic acid.

In one embodiment, the cancer to be treated using the DCA or obvious chemical equivalent thereof is selected from the group consisting of: non-small cell lung cancer, glioblastoma and breast carcinoma.

In another embodiment, the dichloroacetate, or obvious chemical equivalent thereof, is administered in the form of a pharmaceutical composition comprising dichloroacetate or obvious chemical equivalent thereof and a pharmaceutically acceptable carrier. In yet another embodiment the invention provides a use of dichloroacetic acid or dichloroacetate or obvious chemical equivalent thereof in the preparation of a medicament or pharmaceutical composition for the treatment of cancer, such as a cancer associated with hyperpolarized mitochondria. In yet another embodiment, the dichloroacetate, or obvious chemical equivalent thereof, is administered orally.

In yet another embodiment, the dichloroacetate is administered in a water-based formulation. In one embodiment the water-based formulation of DCA comprises 0.0075 g of DCA/l to 7.5 g of DCA/l). In another embodiment the dichloroacetate or obvious chemical equivalent thereof is administered at a total daily dose of ~25-50 mg/kg bid of dichloroacetate. In another embodiment the dose is 10-100 mg/kg given twice a day is administered to the patient. In one embodiment the dose is 25-50 mg bid.

In another embodiment, the invention constitutes a method for determining whether a cancer is associated with hyperpolarized mitochondria, which would predict its therapeutic response to dichloroacetate or obvious chemical equivalents thereof or similar compounds. In one embodiment such method comprises administering an effective amount of dichloroacetate, or chemical equivalent thereof to a cancer tissue sample from a patient and measuring its apoptosis sensitivity and mitochondrial membrane potential using confocal microscopy or flow cytometry. This diagnostic test would determine whether the individual patient could benefit from dichloroacetate or other therapies that cause apoptosis through similar mechanism.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A, B and C are confocal images of cancer and normal cells stained with dyes for mitochondrial membrane potential or antibodies to cytochrome c and apoptosis inducing factor (AIF) as explained in Example 1.

FIG. 1D shows the results of an assay measuring production of hydrogen peroxide ($H_2O_2$) in cancer cells treated with dichloroacetate, as explained in Example 1.

FIGS. 2A and B show patch clamping data in cancer and normal cells in response to dichloroacetate and a variety of inhibitors, as explained in Example 2.

FIG. 2C shows the results of quantitative reverse transcriptase polymerase chain reaction (qRT-PCR) and immunoblotting, studying the expression of Kv1.5 in cancer cells treated with dichloroacetate, as explained in Example 2.

FIG. 3A are confocal images of cancer cells loaded with the calcium-sensitive dye Fluo-3 and mean data for calcium levels, as explained in Example 3.

FIG. 3B are confocal images of cancer cells treated with antibodies against Kv1.5 and NFAT, as explained in Example 3.

FIG. 4A are confocal images of cancer cells assayed for Annexin, TUNEL, PCNA, BrdU and survivin, as explained in Example 4.

FIG. 4B are immunoblots in cancer cells for expression and activity of caspase 3 and 9, as explained in Example 4.

FIG. 5A are representative pictures of explanted tumors and MRI images from the tumors in vivo, as well as a plot of tumor size over time in response to dichloroacetate, as explained in Example 5.

FIG. 5B are confocal images of tumors stained for TUNEL and PCNA as well as mean data, as explained in Example 5.

FIG. 5C are confocal pictures of tumors stained with survivin and Kv1.5 as well as an immunoblot for survivin and Kv1.5, as explained in Example 5.

FIG. 5D illustrates mean data from qRT-PCR analysis for survivin and Kv1.5, plotted over histological grade score, from non small cell cancer of the lung specimens from 30 patients, as explained in Example 5.

DETAILED DESCRIPTION OF THE INVENTION

"Dichloroacetate (DCA) or obvious chemical equivalent thereof" means dichloroacetate acid or salt thereof or other analog, derivative of dichloroacetate that has the same desired therapeutic effect in the treatment of cancer.

For example, salts of dichloroacetic acid are well known and commercially available. Generally, such salts of dichloroacetic acid will have the following formula:

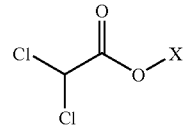

X = Na, K+, CH3 or OH

Specific salts include those formed by the alkali metal and alkaline earth metal ions such as sodium, potassium, calcium, and magnesium, ammonium, and substituted ammonium where the substituent is a mono- or di-lower alkyl radical of 1-4 carbon atoms and ethylene diammonium. Pharmaceutically acceptable salts, with minimum cell cytotoxicity, such as sodium, are preferred.

Specific pharmaceutical salts useful in this invention include sodium dichloroacetate, potassium dichloroacetate, and diisopropyl ammonium dichloroacetate. The sodium dichloroacetate and free base forms are highly preferred. Generally, salt and free base forms of dichloroacetate are particularly preferred for use in the invention because of their ready availability and economical price. In one embodiment, salts of dichloroacetic acid can be used at a concentration between about 0.5 mM to about 100 mM, preferably about 50 mM. Preferably such compounds are used at a concentration of at concentrations of 0.1-10 mM, more preferably at least about 0.5 mM (estimated drug concentration at tumor based on cell culture studies).

"Administering to the cell" as used herein, means any mode wherein a substance is administered to the cell (in vivo or in vitro) and has an effect on said cell, such methods are known to those skilled in the art. By way of example, in vitro, it can be administered to the cell media, or cell culture media. In vivo, by way of example, it can be administered through known forms of pharmaceutical administration.

Figure 5:
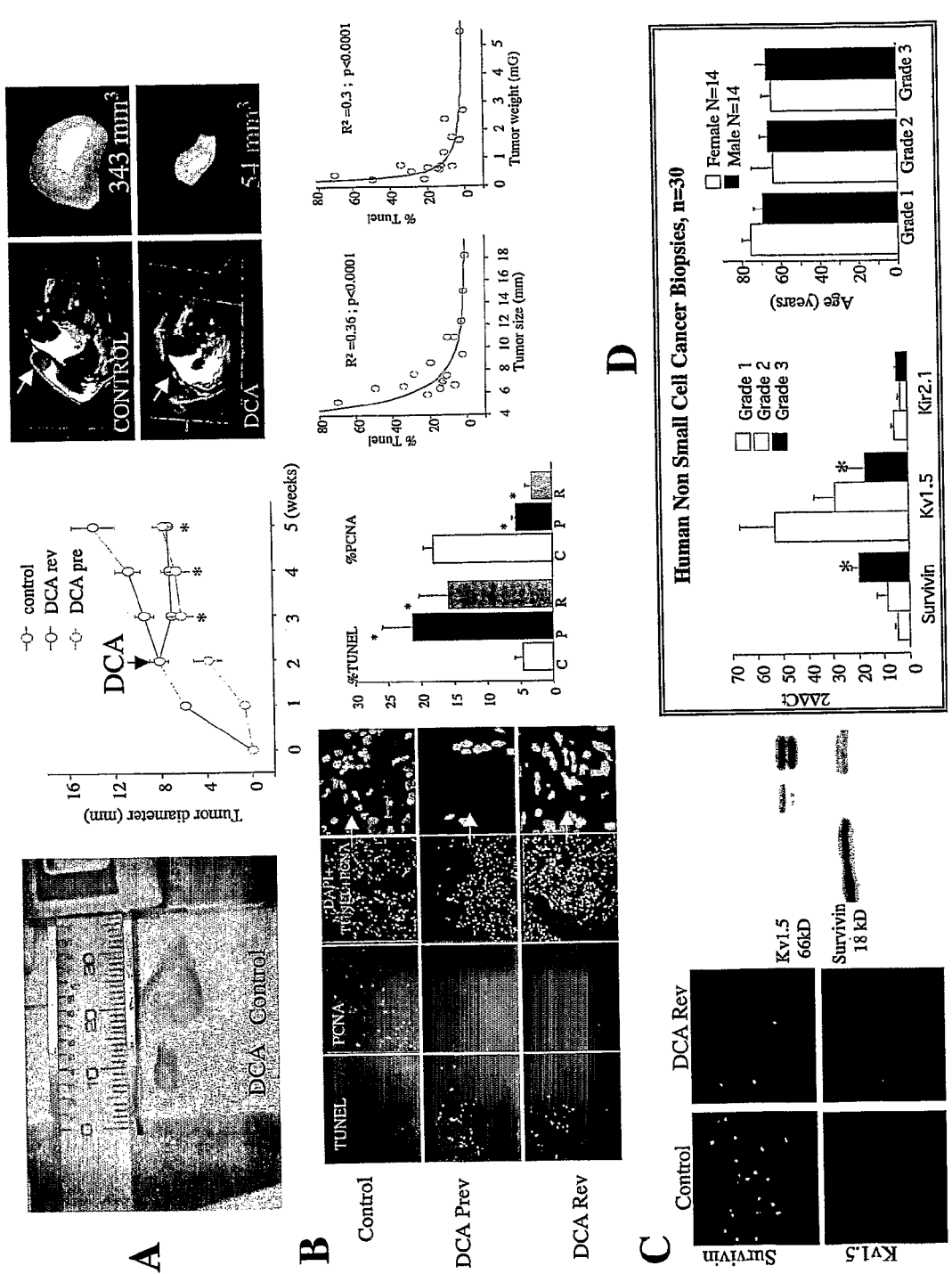
FIG. 5 shows that dichloroacetate prevents and reverses tumor growth in vivo in rats and a similar correlation between apoptosis-K+ channels and malignancy grade in human cancers.

A "patient in need thereof" as used herein is a patient that has or is suspected of having a cancer, such as lung cancer, glioblastoma or breast cancer, which is characterized by apoptosis resistance and/or hyperpolarized mitochondria. Preferably said patient is a mammal, and in one embodiment a human. It is acknowledged that because of the difficulty obtaining human tissue to allow direct measurement of hyperpolarized mitochondria that one could measure survivin (as a surrogate of mitochondria dependent apoptosis) and Kv1.5 mRNA. As shown in FIG. 5 this index of survivin/Kv1.5 is high in all tumor cell lines tested and in a cohort of 30 patients with non-small cell lung cancer. Furthermore DCA reversed this index in vitro and in vivo. Therefore in one embodiment of the invention this index can be used clinically to select the patients most likely to benefit from DCA therapy. However, the method of the invention is not necessarily restricted to such patients as clinical trials using DCA therapy could be used to identify patients who may benefit from the therapy in whom the index is unknown, unavailable or low.

As such, in one embodiment, the invention provides a method for determining whether a cell, or patient comprising cells suspected of being cancer cells can benefit from dichloroacetate or obvious chemical equivalent treatment.

In one embodiment, the invention provides a method for identifying cells or a patient that may benefit from treatment with dichloroacetate or obvious chemical equivalent thereof to induce or reverse resistance to apoptosis and/or to treat cancer, comprising:
  (i) obtaining a cell sample, tissue sample, or sample comprising cancerous cells or cells suspected of being cancerous;
  (ii) administering to said sample dichloroacetate or obvious chemical equivalent thereof;
  (iii) determining whether said apoptosis is induced and/or apoptosis resistance is reversed in said sample,
wherein when said apoptosis is induced and/or apoptosis resistance is reversed in said sample, this is indicative that the cells and/or patient from where the sample was obtained may benefit from dichloroacetate or obvious chemical equivalent treatment.

In one embodiment, the method of determining whether said apoptosis is induced and/or reversed or whether a patient or cell may benefit from dichloroacetate or obvious chemical equivalent treatment is by monitoring the samples survivin/Kv1.5 index. This can be monitored with respect to an external or internal control. For instance, in one embodiment, the index is compared to a pre-determined level or range that is known to benefit from treatment, and/or the index is obtained from the sample prior to treatment and if it is lowered or reversed, then the cell or patient may benefit from treatment.

The dichloroacetate and obvious chemical equivalents of the invention may be formulated into pharmaceutical compositions for administration to humans in a biologically compatible form suitable for administration in vivo. By "biologically compatible form suitable for administration in vivo" is meant a form of the substance to be administered in which any toxic effects are outweighed by the therapeutic effects.

Administration of a therapeutically effective amount of the pharmaceutical compositions or DCA or obvious chemical equivalents thereof of the present invention is defined as an amount effective, at dosages and for periods of time necessary to achieve the desired result. For example, a therapeutically active amount of a substance may vary according to factors such as the disease state, age, sex, and weight of the individual, and the ability of dichloroacetate or obvious chemical equivalent thereof or formulation comprising thereof to elicit a desired response in the individual. The dosage regime may be adjusted to provide the optimum therapeutic response. For example, several divided doses may be administered daily or the dose may be proportionally reduced as indicated by the exigencies of the therapeutic situation.

Accordingly, the present invention provides a pharmaceutical composition for treating a patient in need thereof, such as a human, comprising dichloroacetate or obvious chemical equivalent thereof of the invention and a pharmaceutically acceptable carrier, diluents or excipients.

The term "treating a human" as used herein means administering the pharmaceutical composition of the invention to a human to prevent, alleviate or cure a cancer.

The compositions described herein can be prepared by per se known methods for the preparation of pharmaceutically acceptable compositions which can be administered to subjects, such that an effective quantity of the active substance is combined in a mixture with a pharmaceutically acceptable vehicle.

In one embodiment, the pharmaceutical compositions may be used in methods for treating humans. The dosage and type of dichloroacetate of the invention to be administered will depend on a variety of factors, which may be readily monitored in human subjects. Such factors include the type and severity of the disease.

A further aspect of the present invention relates to methods for therapeutic treatment of humans using dichloroacetate compositions or obvious chemical equivalents thereof.

In a further embodiment of the invention, the dichloroacetate or obvious chemical equivalent thereof can be administered in combination with other pro-apoptotic or chemotherapeutic agents. "In combination with" as used in this context means that the agents can be administered at the same time or at different times, but in a combination treatment regimen, such as combination regimens known to those skilled in the art. In one embodiment, the agents can be formulated into a single or different pharmaceutical compositions.

It is further understood that the therapeutic compositions of the invention may be used in conjunction with pharmaceutically acceptable excipient or carriers. The pharmaceutical compositions according to the present invention are prepared conventionally, comprising substances that are customarily used in pharmaceuticals, [e.g. Remington's Pharmaceutical Sciences (Alfonso R. Gennaro ed. 18th edition 1990), Remington's Pharmaceutical Sciences (Remington's Pharmaceutical Sciences, Mack Publishing Company, Easton, Pa., USA 1985) or Remington's The Sciences and Practice of Pharmacy, 21st Edition (University of the Sciences in Philadelphia, 2005) or Handbook of Pharmaceutical Additives (compiled by Michael and Irene Ash, Gower Publishing Limited, Aldershot, England (1995))], including excipients, carriers, adjuvants and buffers. The compositions can be administered, e.g. orally, parentally, enterally, intramuscularly, subcutaneously, intravenously or other routes useful to achieve an effect. For example, in one embodiment, the active substance may be administered in a convenient manner such as by injection (subcutaneous, intravenous, intramuscular, etc.), oral administration or inhalation. Depending on the route of administration, the active substance may be coated in a material to protect the compound from the action of enzymes, acids and other natural conditions which may inactivate the compound. Conventional excipients include pharmaceutically acceptable organic or inorganic carrier substances suitable for parenteral, enteral, oral and other routes of administration that do not deleteriously react with the agents. For parental application, particularly suitable are injectable sterile solutions, preferably oil or aqueous solutions, as well as suspensions, emulsions or implants, including suppositories. Ampules are convenient unit dosages. The pharmaceutical preparations can be sterilized and, if desired, mixed with stabilizers, wetting agents, emulsifiers, salts for influencing osmotic pressure, buffers or other substances that do not react deleteriously with the active compounds. In one embodiment, the pharmaceutical compositions of the invention are compositions that can be administered orally.

The invention will now be described by the following non-limiting examples.

EXAMPLES

Methods

Cell Culture:

The non-small cell lung cancer cell line A549, the glioblastoma cell line MO59K, and the mammary carcinoma cell line, MCF 7, were purchased from ATCC (VA USA). Normal small airway epithelial cells (NSAEC) were purchased from Cambrex Bio-science. A549 were maintained on F12K medium, glioblastoma on DMEM/F12, (Gibco/Invitrogen ON Canada), MCF-7 cells on DMEM (Sigma-Aldrich, ON Canada) and NSAEC on special small airway epithelial cell basal medium provided by the company. All media were supplemented with 10% FBS (Sigma-Aldrich) and 5% PSF (Gibco) as antibiotic.

Tumorigenicity Assays in Nude Rats.

Cells from A549 cell lines were harvested and resuspended in PBS. The cell suspension (3.106 cells per injection) was injected s.c. in the back (below the scapula level) of athymic nude rats. Rats were randomly divided into 3 groups: control (received only the cells at day 0), DCA prevention group (cells+DCA at day 0) and DCA reversal (cells at day 0+DCA 2 weeks post injection). The DCA 0.075 g/L was added to the drinking water and the rats had free access to water. At this dose the DCA solution is colourless and odorless. Rats were observed weekly for the visual appearance of tumors at injection sites, and tumor sizes were measured every week in the 3 groups during one month. At the end of the month, rats were killed, and the tumors were excised and fixed for apoptosis and proliferation measurements. Some tumors were imaged in anesthetized rats with A SIEMENS 1.5T MRI system, using standard sequences, allowing for 3D reconstruction and calculation of the tumor volume in vivo.

Immunoblotting:

Antibodies to $K^+$ channels were purchased from Alomone (Jerusalem, Israel). Cells or tumor were collected and immunoblotting was performed on pooled samples from 4 T-25 dishes or 4 rats in each of the 2 groups (25 µg protein in pooled sample/lane), as previously described. The films were digitized and quantitated using 1D Image Analysis Software (Kodak, Rochester, N.Y.). Expression was normalized to both Ponceau-S and smooth muscle actin signal to correct for loading differences.

qRT-PCR:

Samples were added to a microwell plate with TaqMan probes and RT-PCR reagents (Applied Biosystems, Foster City, Calif.). qRT-PCR was performed with an ABI PRISM 7700 Sequence Detector (Applied Biosystems) and primers for human Kv1.5, survivin, 18s and Beta 2 microglobulin as described.

Electrophysiology:

Whole cell electrophysiology was performed on cultured cells. Cells were voltage-clamped at a holding potential of −70 mV. Currents were evoked by 200-ms test pulses from −70 to +70 mV filtered at 1 kHz and sampled at 2-4 kHz.

Confocal Microscopy:

Imaging was performed using a Zeiss LSM 510 confocal microscope as described. Apoptag apoptosis detection kit (TUNEL stain, Serologicals, Norcross, Ga.) and the proliferating cell nuclear antigen (PCNA) antibody (DAKO, Carpinteria, Calif.) were used as per manufacturer's instructions on both formaldehyde fixed cells and paraffin-embedded tissue sections after antigen retrieval. Nuclear staining was made using 4',6'-diamidino-2-phenylindole dihydrochloride (DAPI, 300 nM; Molecular Probes) in fixed tissue or cells as previously described Apoalert Annexin V kit (Clontech, Palo Alto, Calif.), cytochrome c antibody (Pharmingen, San Diego, Calif.), Apoptosis inducing factor (Santa Cruz Calif. USA) NFAT and Kv1.5 (Sigma) and mitotracker red (500 nM, Molecular Probes) were used as described by the company instructions. Mitochondrial membrane potential ($\Delta\Psi m$) was studied in live cancer cultured cells, using tetramethylrhodamine methyl-ester perchlorate (TMRM) (20 nmol/L) for 30 minutes (37° C.) and Hoechst (1.0 umol/L) nuclear staining for 10 minutes (Molecular Probes, Canada).

$H_2O_2$ Measurements.

Cancer cells were propagated on LabTek multiwell slides (Nalgene/Nunc, VWR, ON Canada) until confluent. Monolayers were pre-incubated with 500 µM DCA (Sigma-Aldrich) in the presence or absence of 5 µM rotenone (Sigma-Aldrich) for one hour. Production of $H_2O_2$ was measured by Amplex Red (Molecular Probes, Eugene Oreg.) following the manufacturer's recommendations over a one hour period in the presence of the relevant drug(s). Fluorescence was measured at 590 nm with excitation at 530 nm and $H_2O_2$ levels determined by reference to a standard curve. Each assay was done four times.

DNA Microarrays:

Total RNA from A549 and MO59K treated (DCA 500 µM for 48H) and untreated cells were extracted using Quiagen RNeasy kit (Ontario, Canada). Differences in genes expression between control A549, MO59K and DCA-A549, DCA-MO59K cells was assessed using human DNA chip set U133A (Affymetrix, California, USA). Analysis was performed using Affymetrix software. Changes in gene expression were considered significant only if the expression was altered by ≥1.75 fold. Special intention was made on genes that were change in both A549 and MO59K. Then a pathway analysis (GO analysis) was performed.

Statistics:

Values are expressed as the mean±SEM. Inter-group differences were assessed by Kruskal Wallis or One-way ANOVA as appropriate with post hoc analysis using Fisher's Exact Test (Statview 4.02, SAS Institute, Cary, N.C.).

Example 1

Figure 1:
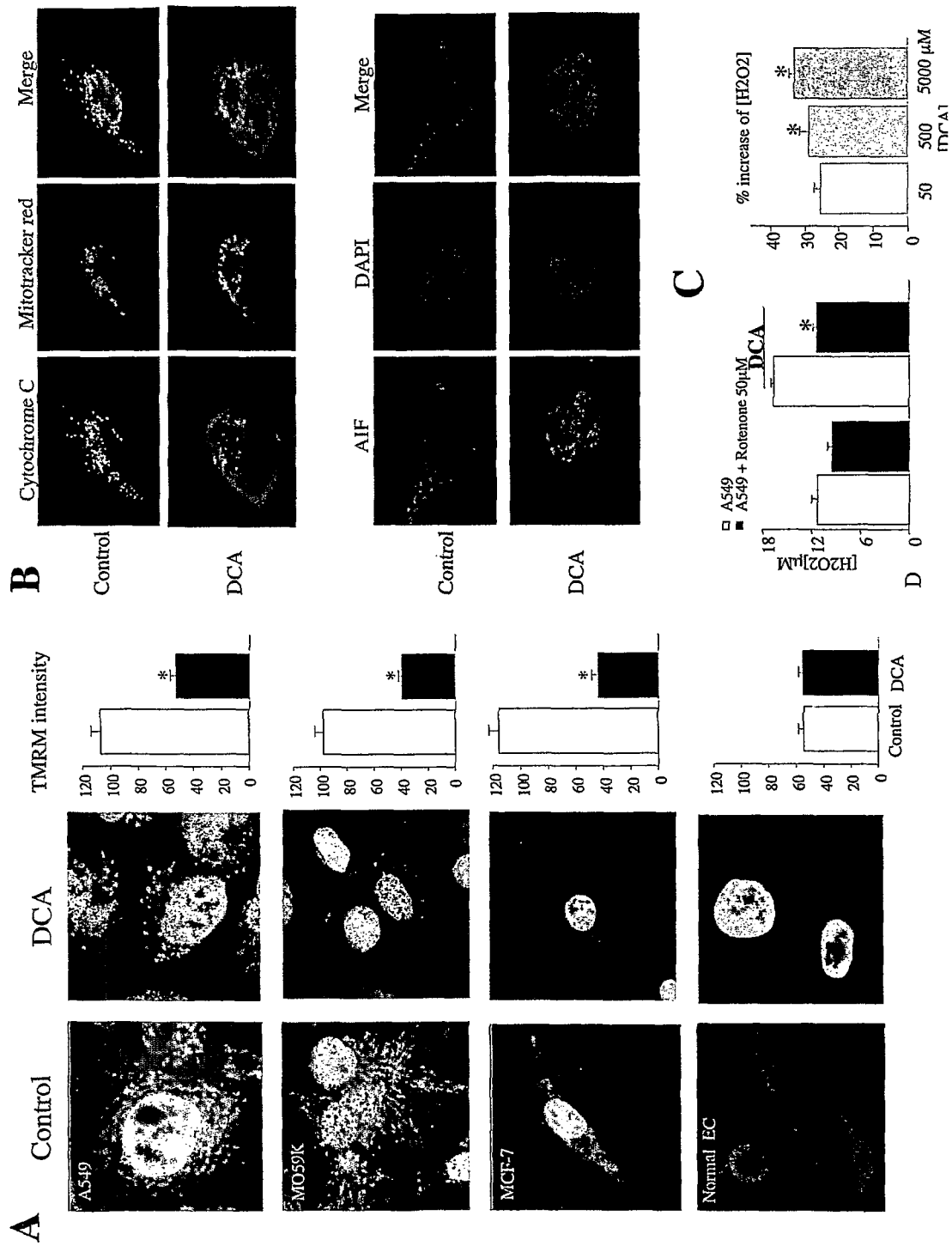
FIG. 1 shows that dichloroacetate depolarizes mitochondria, releases cytochrome-c and AIF from the mitochondria and enhances $H_2O_2$ production.

DCA Depolarizes Mitochondria, Releases Cytochrome-c and AIF from the Mitochondria and Enhances $H_2O_2$ Production (FIG. 1)

A: 48H of DCA (500 µM) significantly depolarized the mitochondria in A549, MO59K, MCF-7 cancer cells, but had no effect on normal epithelial cells (EC).

B: In the upper panel, cytochrome-c in green is co-localized with the mitotracker red staining in control, whereas after 48H DCA cytochrome-c leaked out the mitochondria and is localized into the cytosol.

C: In control (upper panel) AIF in red is not localized in nucleus, whereas after 48H DCA AIF is mainly localized into the nucleus.

D: DCA increases $H_2O_2$ production in a rotenone and dose-dependent manner.

Example 2

Figure 2:
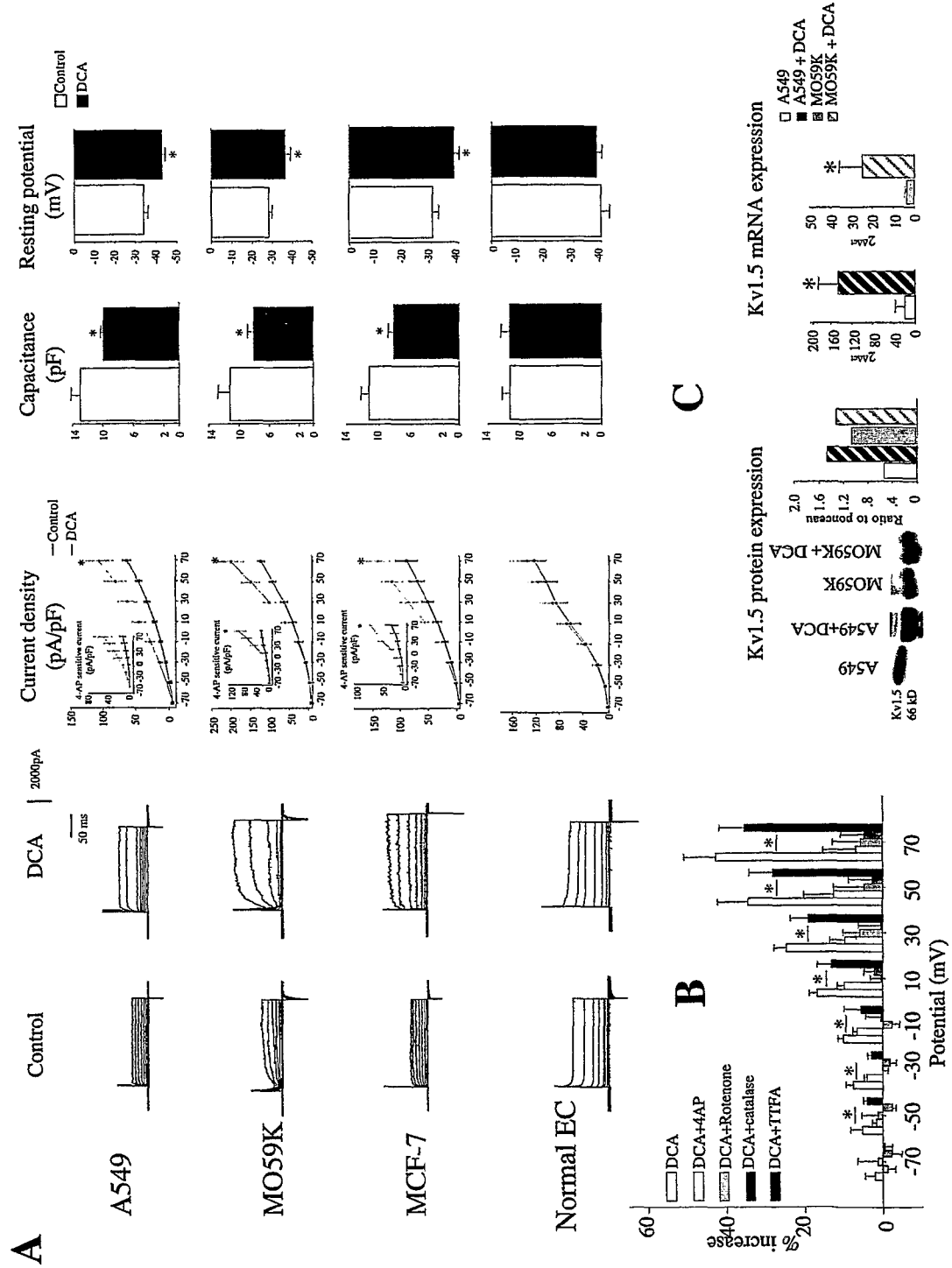
FIG. 2 shows that dichloroacetate increases $K^+$ current and repolarizes cancer cells without affecting normal cells.

DCA Increases K+ Current and Repolarizes Cancer Cells without Affecting Normal Cells (FIG. 2)

A: 48H DCA (500 µM) increases K+ current density in all cancer cells lines (A549, MO59K and MCF-7) but does not affect normal cells such as the normal epithelial cells. On the right, original traces representing the K+ current in both control (untreated cells) and DCA treated cells. Increase in K+ current density was mainly due to an increase in Kv current, as shown by the 4-AP-sensitive current in the legend. Increased K+ current density results in a significant decrease in membrane capacitance, (which suggests a decrease in cell volume) and repolarization of the resting membrane potential.

B: The mechanism by which DCA increases K+ current was assessed by cancer cells acutely exposed to DCA (10 min, 500 µM). The effects of DCA on K+ current were blocked by 4-AP and blocked by both catalase and rotenone (50 µM). TTFA, a specific blocker of complex II did not prevent the effects of DCA.

C: DCA treated cells (48 hrs) had increased Kv1.5 protein and mRNA, suggesting that DCA is able to increase Kv channel expression.

Example 3

Figure 3:
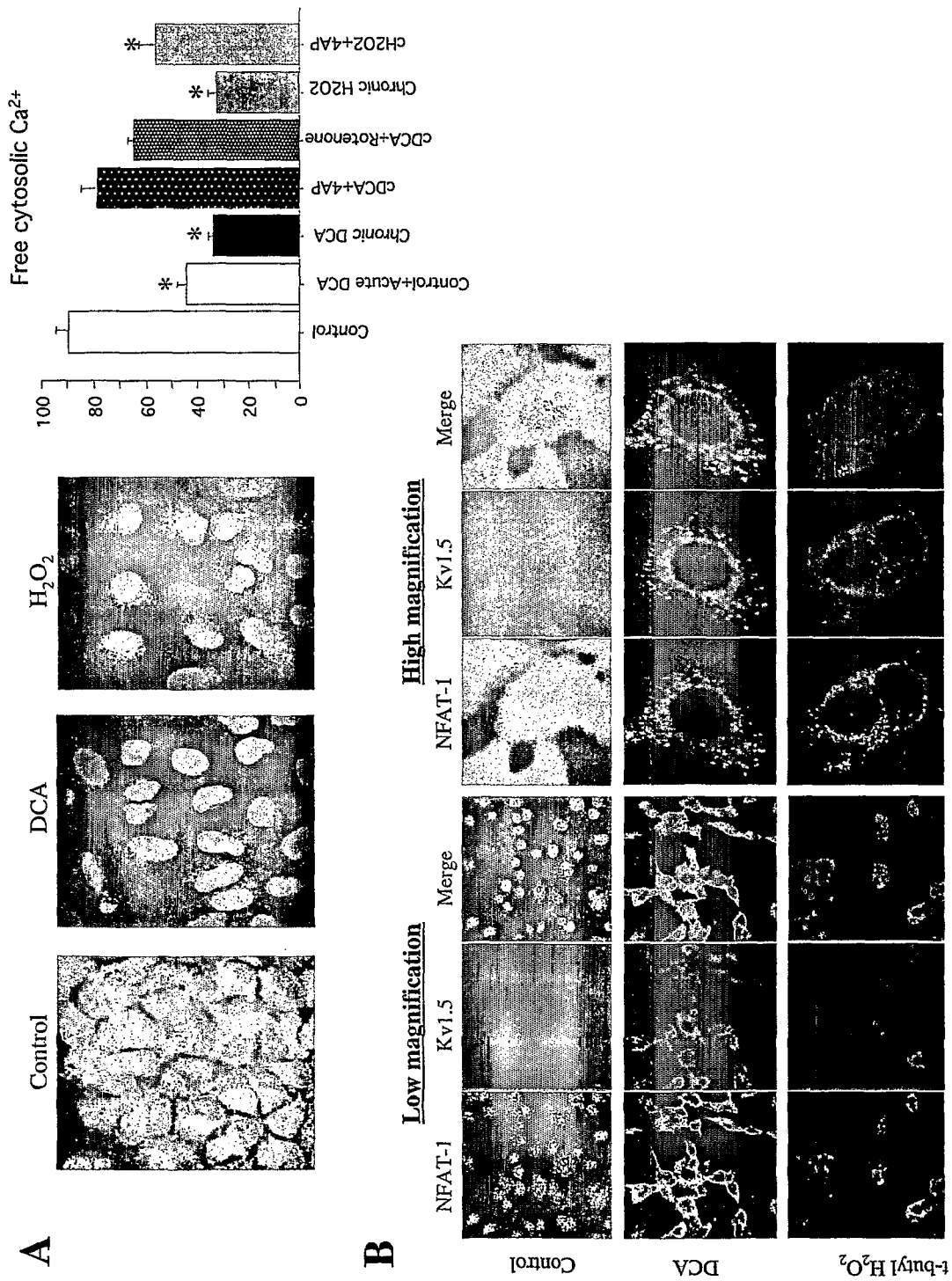
FIG. 3 shows that DCA increases Kv1.5 expression via the Ca++/calcineurin-dependent transcription factor NFAT.

DCA Increases Kv1.5 Via the
Ca++/Calcineurin-Dependent Transcription Factor
NFAT (FIG. 3)

A: Free cytosolic calcium concentration was measured using fluo-3. Control cells had more calcium than both DCA and $H_2O_2$ treated cells. Acute DCA decreased the calcium concentration through a 4-AP and rotenone sensitive pathway confirming the electrophysiology data.

B: Confocal imaging of A549 cells showed that NFAT (green) is activated as it is mainly localized in the nucleus of most of the untreated cells. Interestingly, these cells had a very low level of Kv1.5 expression (red). Both DCA and $H_2O_2$ blocked the activation of NFAT as shown by its localization out of the nucleus in the cytoplasm, and had increased Kv1.5 expression.

Example 4

Figure 4:
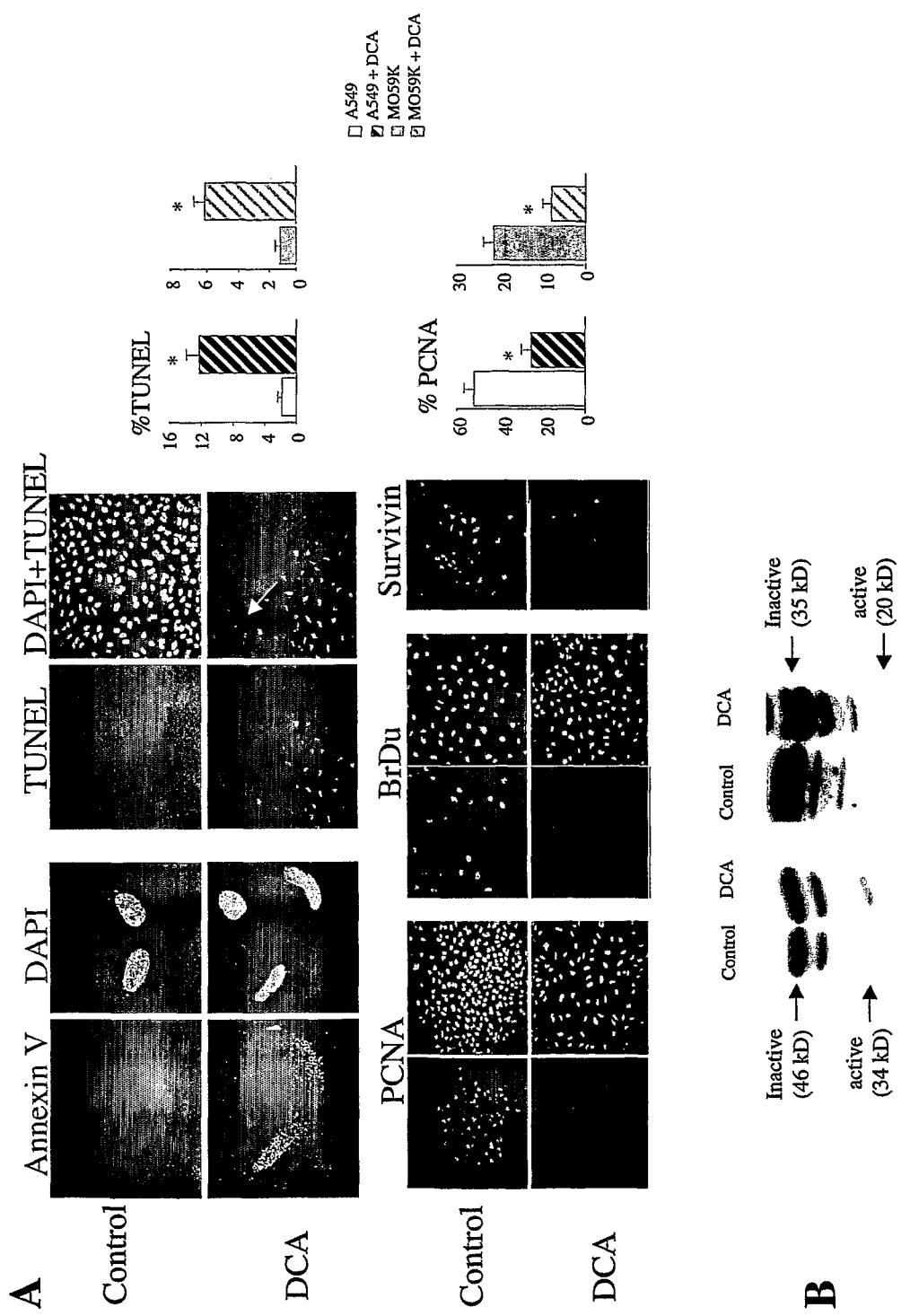
FIG. 4 shows that dichloroacetate increases apoptosis and decreases proliferation of cancer cells in vitro.

DCA Increases Apoptosis and Decreases
Proliferation of Cancer Cells in Vitro (FIG. 4)

A: DCA significantly increases apoptosis as a higher number of DCA treated cells are Annexin V positive and TUNEL positive. DCA also significantly decreases proliferation as less DCA treated cells were positive to PCNA, BrDU or survivin.

B: Increased apoptosis is also shown by the DCA-induced activation of both caspase 3 and 9 as immunoblots reveal an active band for both caspases.

Example 5

DCA Prevents and Reverses Tumor Growth in Vivo
(FIG. 5)

A: Injection of A549 cells into the flank of nude rats induced the development of tumor within a week. DCA treated rats in both prevention and reversal protocols had smaller tumors. The size of tumors were assessed by caliper as shown on the picture, by weight and by using MRI in vivo.

B: DCA treated rats had tumors with an increase in apoptosis as shown by TUNEL. Interestingly a significant negative correlation was observed between % TUNEL and both tumor size and weight.

C: As in the in vitro experiments, DCA increased Kv1.5 expression and decreased survivin expression in vivo. Representative confocal immunohistochemistry is shown on the left and immunoblotting on the right. The 2 lanes on the left are from non treated rats while the right 2 lanes are from DCA-treated rats.

D: Human non-small cell lung cancers show a positive correlation between histological grade and the survivin/Kv1.5 index (the higher the tumor grade the more aggressive the tumor).

Results and Discussion

Human A549 (non small cell lung cancer), MO59K (glioblastoma) and MCF-7 (breast cancer) cancer cells have hyperpolarized mitochondria; DCA treatment induces Δψm depolarization, mitochondrial release of both AIF and cytochrome C and increases mitochondrial $H_2O_2$ production (FIG. 1). TMRM (tetramethylrhodamine methyl-ester) is a positively charged dye that accumulates in the negatively charged mitochondria in a mitochondria membrane potential-dependent manner, i.e. the more the red signal of TMRM the more hyperpolarized the mitochondria. All cancer cell types have more red fluorescence, i.e. they were more hyperpolarized than the normal epithelial cells (EC) at the bottom. Hyperpolarized mitochondria reflect an apoptosis resistance state, since it is mitochondrial depolarization that initiates apoptosis. DCA depolarizes mitochondria in all the cancer cell types. DCA did not alter the mitochondrial membrane potential in normal human lung epithelial cells (FIG. 1). Interestingly, DCA brought the mitochondria membrane potential to the level of the normal epithelial cells. Together these findings likely explain the relative lack of toxicity of DCA on normal tissue and should confer a wide therapeutic window to this cancer treatment strategy. The mitochondrial depolarization was associated with the release from the mitochondria of both apoptosis inducers, cytochrome-c and apoptosis inducing factor (AIF). Cytochrome c leaks to the mitochondria and activates caspases, the effectors of apoptosis. AIF is translocated to the nucleus where it initiates caspase-independent apoptosis. DCA treatment of all A549, MCF-7 and MO59K causes leakage of cytochrome c to the cytoplasm and translocation of AIF to the nucleus, as shown by the multiple immunostaining and confocal imaging in FIG. 1B. The cells were stained green with a monoclonal antibody to cytochrome c and red with mitotracker red, a mitochondrial marker. The green staining in control was confined to discrete areas (mitochondria) whereas in the DCA-treated cells it diffusely stains the cytoplasm. The cells were stained red with AIF antibody and blue for DAPI a nuclear marker. The red staining in control was confined in the cytosol whereas in the DCA-treated cells it stains in the nucleus. An opening of the mitochondrial transition pore (MTP) is required for both cytochrome c and AIF release and this is associated with mitochondrial depolarization in mitochondria-dependent apoptosis.

A major stimulus of the redox-sensitive MTP is an increase in the production of activated oxygen species (AOS) produced in the electron transport chain of the mitochondria. AOS production is increased as the mitochondrial depolarize. Due to the presence of MnSOD in the mitochondria, superoxide is dismutated to $H_2O_2$, a radical that is relatively stable and can leak in the cytoplasm and the plasma membrane, where it can affect redox-sensitive mechanism, including the opening of $K^+$ channels.

Exposure to DCA (50, 500 and 5000 µM) for 4 hours increased $H_2O_2$ production in A549 cells in a dose-dependent manner. The effect of DCA was totally inhibited by rotenone, a complex I inhibitor, suggesting that most of free radical used to produce $H_2O_2$ was produced in the complex I (FIG. 1C).

Chronic DCA Treatment Increases Kv Current Density and Hyperpolarizes the Plasma Membrane (FIG. 2).

As illustrated in FIG. 2A, Kv1.5 has been implicated in the mechanism for apoptosis, at least in pulmonary artery smooth muscle cells. Increase in both Kv1.5 expression and current density was responsible of decreased $[K+]_i$ leading to shrinkage of the cells and a decrease in the tonic inhibition that $K^+$ exerts on caspases, thus promoting apoptosis. In the cancer cells of the present examples, there was a significant increase in $K^+$ current in DCA treated cells, compared to the cancer untreated cells. Most of the increased $K^+$ current in the DCA treated cells is 4-aminopyridine sensitive (i.e. Kv current).

The DCA-Induced Activation of Kv Channels is Due to the Increase in the $H_2O_2$ Production (FIG. 2C).

In order to determine the mechanism of the increase in the Kv current, pharmacology experiments were performed on the acute effect of DCA on cancer cells. DCA (500 µM) superfused over A549 cells for 5 to 10 minutes also caused an increased $K^+$ current, similar to that caused by chronic exposure to DCA. The effect of DCA on $K^+$ current was blocked by both catalase and rotenone (10 µM) but not by TTFA (50 µM, an inhibitor of complex II of the electron transport chain), suggesting that $H_2O_2$ derived from complex I, but not complex II, was responsible for the Kv current activation (as it was fully blocked by 4-AP).

DCA Upregulates the Kv1.5 Expression Via a [Ca++]i-NFAT Pathway (FIG. 3).

In addition to the acute activation of existing Kv channels, DCA might increase the outward $K^+$ current by upregulating the expression of the Kv1.5 protein. In fact, downregulation of Kv1.5 might be a feature of the cancer cells, contributing to the resistance to apoptosis of cancer cells. Both mRNA and protein levels of Kv1.5 channels were increased in DCA treated cells compared to the controls in agreement with the electrophysiology data (FIG. 2C). The transcription factor NFAT is regulated by intracellular calcium and calcineurin. Increase in the intracellular $Ca^{++}$ activates calcineurin, which de-phosphorylates NFAT, allowing its translocation to the nucleus, where it decreases Kv1.5 expression. Since the DCA hyperpolarized the plasmalemmal membrane, it is very likely that the influx of $Ca^{++}$ via voltage gated $Ca^{++}$ channels will decrease. Cells were studied using confocal microscopy and Fluo-3. DCA treated cells had a significant decrease of the [C++] compared to the untreated cells (FIG. 3A). Decreased [Ca++] induced by DCA was blocked by both 4-AP and rotenone, reinforcing the hypothesis that complex I-produced $H_2O_2$ activated Kv channels and thus repolarized the membrane potential. Furthermore, exogenous $H_2O_2$ mimics the effect of DCA and decreases the intracellular Ca++ levels (FIG. 3A). As expected, in the untreated cancer cells, NFAT was localized in the nucleus whereas in both DCA and $H_2O_2$ treated cells NFAT was localized in the cytosol (FIG. 3B). Interestingly, when cells had a nuclear localization of NFAT they expressed very little Kv1.5, studied by co-staining with an antibody to NFAT and Kv1.5 and DAPI staining for imaging of the nucleus (FIG. 3B).

The data showed that DCA depolarizes mitochondria and causes the release of pro-apoptotic mediators. Furthermore, the increase in Kv current (acutely via the production of $H_2O_2$ and chronically via the NFAT mediated increase in Kv1.5 expression) would further potentiate apoptosis more distally in the pathway, via the decrease in the K+-induced caspase inhibition. Thus, with a "double hit" mechanism, DCA would be a powerful inducer of apoptosis and reverse both causes of potential resistance to apoptosis, i.e. mitochondrial hyperpolarization and Kv inhibition. Apoptosis was then measured with a number of assays. The apoptosis-resistance cells would actually be the ones proliferating the most. Therefore, by eliminating these cells, DCA will likely decrease indices of cell proliferation in the cancer cells; for this reason indices of cell proliferation was also measured.

The DCA-Induced Apoptosis is Mitochondria-Dependent, and Occurs Early (FIG. 4).

DCA treatment (500 µM) of A549 cells causes early induction of apoptosis as evidenced by the annexin V staining, which stains phosphatidylserine expressed early on the surface of apoptotic cells (FIG. 4A). Non-treated cells showed almost no apoptosis (measured by TUNEL) and significant cell proliferation (measured by PCNA, BrDu and DAPI counting) (FIG. 4A). In contrast, DCA-treated cells showed a significant increase in apoptosis and a decrease in cell proliferation (FIG. 4A). Shrunk and pyknotic nuclei, a feature of late apoptosis, were seen in the apoptotic cells. Both the caspase-3 and 9 activity was as well enhanced in DCA treated cells (FIG. 4B). In addition, DCA treatment decreased the expression of survivin, an inhibitor of apoptosis protein that is selectively expressed in cancer (FIG. 4A). Survivin expression is considered an index of poor prognosis in a large number of cancer types.

Since DCA decreases proliferation and increases apoptosis without affecting normal cells, it would be beneficial in the treatment of cancer in vivo.

DCA Blocks Tumor Growth in Nude Rats (FIG. 5)

Nude rats were injected with $3.10^6$ A549 cells. The rats developed tumors within a week. 20 animals were divided into 3 groups: controls did not receive DCA, DCA-prevention rats received DCA just after cell injection for 5 weeks, and DCA-reversal rats received DCA 2 weeks post cell injection for 3 more weeks. The control rats rapidly develop tumor with a constant and exponential tumor growth (FIG. 5A). Both DCA-treated groups had a significant decrease in the tumor size, measured by tumor weight at the time of rat sacrifice, and tumor maximal diameter measured weekly in alive rats using calipers as well as using MRI in alive rats (FIG. 5A). The decrease in the tumor growth in the DCA treated group was associated with an increase in apoptosis (TUNEL) and a decrease in proliferation (PCNA and survivin) (FIG. 5B), confirming the in vitro results. In fact, there was a negative correlation between apoptosis and tumor size (the higher the apoptosis the smaller the size) suggesting that the induction of apoptosis is in fact the mechanism by which the tumor size was decreased (FIG. 5B). In addition, Kv1.5 was upregulated and survivin was downregulated in the treated rats (FIG. 5C), again confirming the in vitro data.

Since survivin is regulating mitochondria-dependent apoptosis, via the mechanism that was described above, the depolarization in mitochondria might eventually cause an up regulation of Kv1.5. Thus survivin and Kv1.5 might be regulated in parallel and together serve as an index of apoptosis resistance in tumors. In order to validate this hypothesis and increase the clinical relevance of the animal data, tissues from 30 patients with non small cell lung cancer were analyzed from the archives of the University of Alberta pathology department. Since all tissues were archived, functional studies (i.e. measure of mitochondrial membrane potential) could not be performed, but survivin and Kv1.5 expression could be measured. The survivin/Kv1.5 ratio index correlated positively with the aggressiveness of the tumor (i.e. the higher the index, the higher the tumor histological grade as assessed by blinded pathologists) (FIG. 5D). The age and the sex of the patients were similar among the 3 standard histological grades. These results validate the relevance of the animal work and for the first time link the mitochondria-dependent apoptosis with the expression of Kv channels, under a comprehensive mechanism offering cancer cells resistance to apoptosis.

Figure 6:
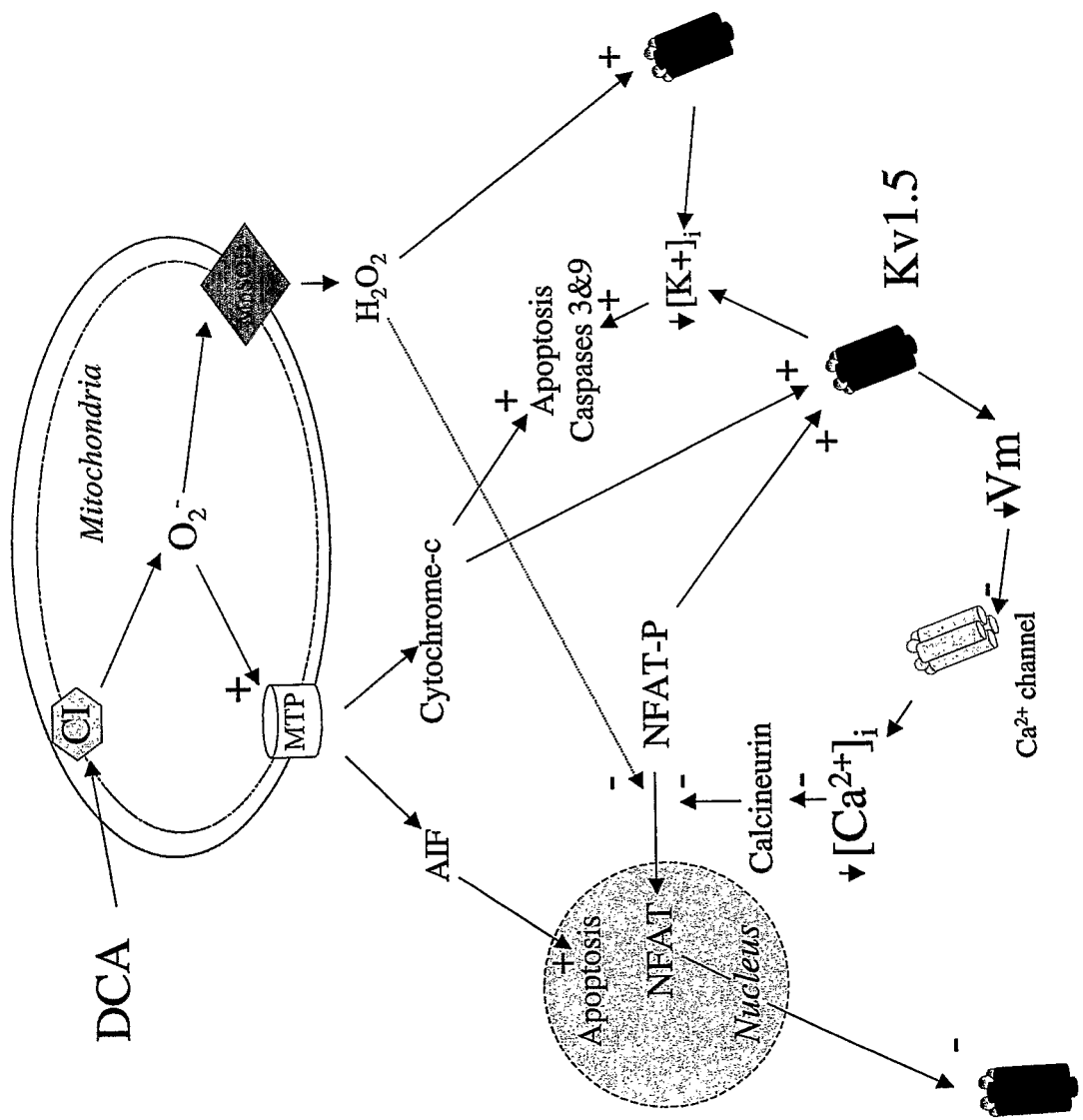
FIG. 6 is a schematic drawing illustrating dichloroacetate's proposed mechanism of action.
Figure 7:
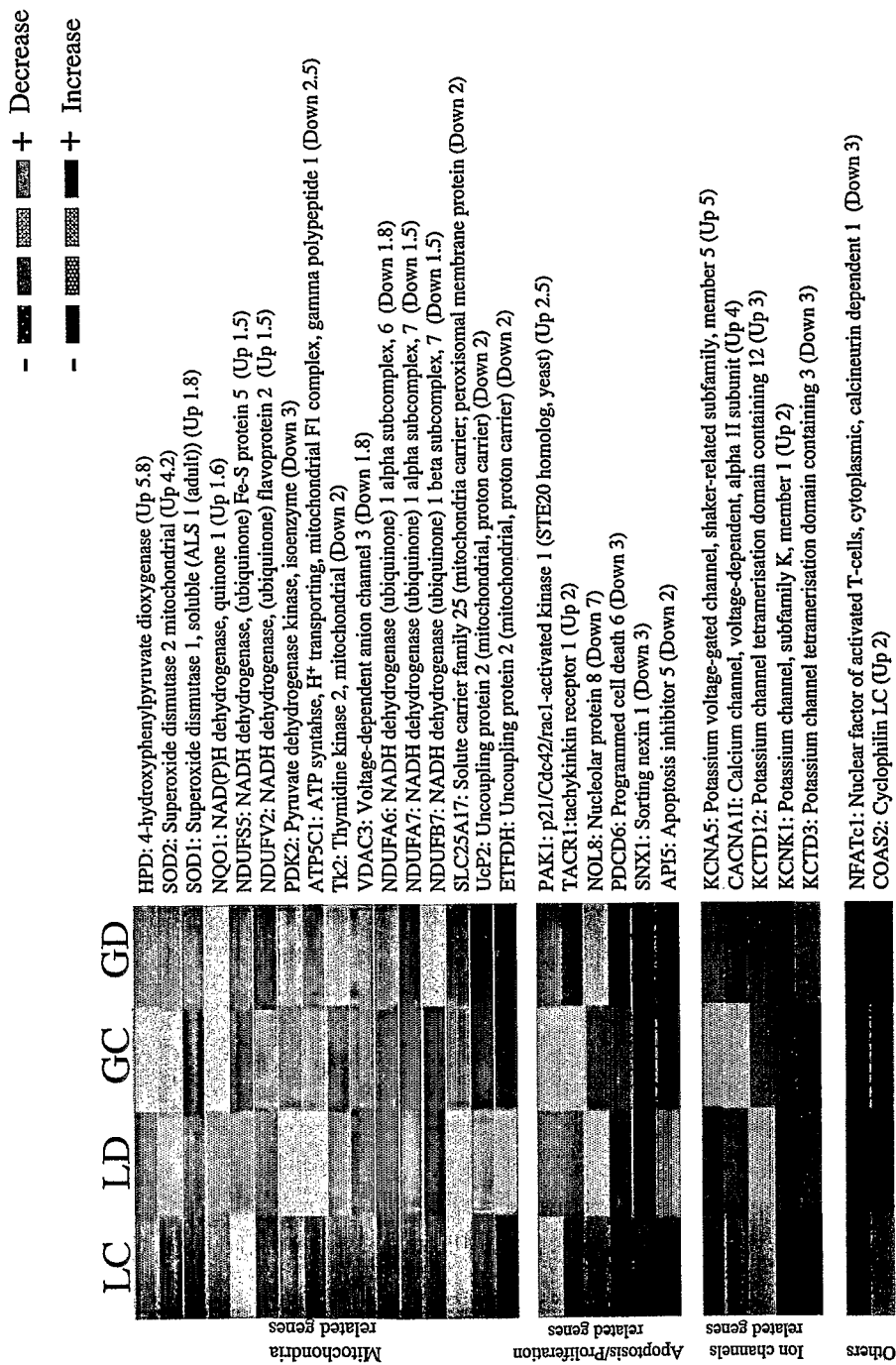
FIG. 7 is a heat map of genes modified by dichloroacetate in cancer cells, using an Affymetrix gene microarray, as explained at the bottom of the results and discussion section.

DCA's Effects are Restricted to Mitochondrial Pathways (FIGS. 6 and 7)

DCA is a prototype inhibitor of the mitochondrial enzyme pyruvate dehydrogenase kinase and thus DCA activates pyruvate dehydrogenase and promotes glucose oxidation. Consequently, DCA increases the delivery of NADH in the complex one of the electron transport chain. This results in an increase in the AOS production within the mitochondrial complex I and the depolarization of mitochondria, initiating apoptosis, as described in the proposed mechanism of action of FIG. 6. In order to confirm that the effects of DCA are not nonspecific but are indeed metabolic and regulate apoptosis pathways, a gene chip and GO analysis of treated and non-treated cells was performed. We used a "subtraction" strategy to reveal relevant changes in tumor gene expression that were solely due to DCA. Studying both the A549 and glioblastoma cell line (i.e. a very different tumor than the lung cancer, epithelial versus glial cells) and focusing on the changes that occurred in a similar pattern in response to DCA therapy revealed changes in gene expression due to DCA, rather than idiosyncratic tumor-specific gene changes.

The genes that were modified by DCA in parallel in A549 (lung) and MO59K (glioblastoma) are listed and their expression levels were plotted in a heat map (FIG. 7). LC=lung cancer cells control, LD=lung cancer cells treated with DCA, GC=glioblastoma cells controls, GD=glioblastoma cells treated with DCA. Most of these genes were related to mitochondria and complex I and interestingly, among all the voltage-gated potassium channels only Kv1.5 was significantly upregulated. This gene chip analysis further supports the model described in FIG. 6.

CONCLUSION

The present study concludes that DCA is an attractive treatment for cancer, such as human cancer. The present invention shows the interplay of mitochondria membrane Kv channels and apoptosis.

In one embodiment, not being bound by a particular mechanism, the positive effects of DCA can potentially be explained by the fact that mitochondrial hyperpolarization and downregulation of K+ channels contribute to the apoptosis resistance state that characterizes cancer. In one embodiment, DCA increases the delivery of NADH in the mitochondrial ETC complex I, resulting in an increase in the production of $H_2O_2$ and mitochondrial depolarization. The mitochondrial depolarization initiates apoptosis by causing a leak of proapoptotic mediators in the cytoplasm. At the same time, the H2O2 can activate the plasmalemmal Kv channels and can activate redox-sensitive transcription factors in the nucleus (our preliminary findings suggest activation of NFAT) and also upregulate Kv1.5 expression. There is strong evidence that shows that DCA only depolarizes mitochondria that are abnormally hyperpolarized. DCA does not change the mitochondrial membrane potential and the K+ current in normal vascular and epithelial cells. This provides the basis for the selectivity of the DCA, i.e. DCA will not affect non-cancerous cells, a highly desirable feature of all candidate cancer therapies. DCA by itself blocks tumor prevention, but by reversing the apoptosis resistance state, DCA would make tumors more sensitive to proapoptotic chemotherapies, decreasing the required doses and toxicities. Metabolic modulators might be a new class of orally available anticancer drugs. The present invention illustrates for the first time that targeting a mitochondria-K+ channel axis is proposed and shown to be effective in cancer.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method for treating a cancer associated with hyperpolarized mitochondria comprising:
   selecting a patient having a cancer comprising hyperpolarized mitochondria and/or an elevated survivin to Kv1.5 protein ratio relative to a normal control; and
   administering to said patient in need thereof a therapeutically effective amount of dichloroacetate (DCA) or an acid or salt thereof.

2. The method of claim 1 wherein the dichloroacetate or acid or salt thereof is a salt of dichloroacetic acid.

3. The method of claim 2 wherein the dichloroacetate or acid or salt thereof is sodium dichloroacetate.

4. The method of claim 1 wherein the cancer comprising hyperpolarized mitochondria and/or an elevated survivin to Kv1.5 protein ratio relative to a normal control is selected from the group consisting of non-small cell lung cancer, glioblastoma and breast carcinoma.

5. The method of claim 1 wherein the dichloroacetate or acid or salt thereof is administered in the form of a pharmaceutical composition comprising dichloroacetate or acid or salt thereof and a pharmaceutically acceptable carrier.

6. The method of claim 1 wherein the dichloroacetate or acid or salt thereof is administered orally.

7. The method of claim 6 wherein 10-100 mg/kg of DCA or acid or salt thereof is administered per day.

8. The method of claim 6 wherein 10-100 mg/kg of DCA or acid or salt thereof is administered twice per day.

9. The method of claim 8 wherein a dose is 25-50 mg/kg.

10. The method of claim 7 wherein a dose is 25-50 mg/kg.

11. The method of claim 1 wherein the dichloroacetate or acid or salt thereof is administered in combination with another pro-apoptotic agent and/or chemotherapeutic agent, and/or other cancer therapy.

12. The method of claim 1 wherein the administering of an effective amount of dichloroacetate or acid or salt thereof induces apoptosis and/or reverses apoptosis resistance in a cancer cell of the patient.

13. The method of claim 1 wherein the administering of an effective amount of dichloroacetate or acid or salt thereof inhibits proliferation of cancer cells of the patient.

14. The method of claim 1 wherein the administering of an effective amount of dichloroacetate or acid or salt thereof decreases level of survivin in a cancer cell of the patient.

15. The method of claim 1 wherein the administering of an effective amount of dichloroacetate or acid or salt thereof increases level of Kv1.5 protein in a cancer cell of the patient.

16. The method of claim 1 wherein the administering of an effective amount of dichloroacetate or acid or salt thereof increases level of apoptosis-inducing factor (AIF) in a cancer cell of the patient.

17. The method of claim 1 wherein the administering of an effective amount of dichloroacetate or acid or salt thereof increases level of $H_2O_2$ in a cancer cell of the patient.

18. The method of claim 1, wherein cancer cells, but not normal or non-cancerous cells, of the patient are affected by the administration of dichloroacetate or acid or salt thereof.

19. The method of claim 1, wherein the dichloroacetate or acid or salt thereof has the formula $CH(Cl_2)-COO-X$, wherein X is selected from the group consisting of $Na^+$, $K^+$, $CH_3$ and OH.

20. The method of claim 1, wherein the dichloroacetate or acid or salt thereof has the formula $CH(Cl_2)-COO^-K^+$.

* * * * *